United States Patent
Henderson

(10) Patent No.: US 12,364,551 B2
(45) Date of Patent: Jul. 22, 2025

(54) MEASUREMENT GUIDED RESURFACING DURING ROBOTIC RESECTION

(71) Applicant: CUREXO, INC., Seoul (KR)

(72) Inventor: Steve Henderson, Fremont, CA (US)

(73) Assignee: CUREXO, INC., Seoul (KR)

( * ) Notice: Subject to any disclaimer, the term of this patent is extended or adjusted under 35 U.S.C. 154(b) by 175 days.

(21) Appl. No.: 17/923,041

(22) PCT Filed: May 11, 2021

(86) PCT No.: PCT/US2021/031703
§ 371 (c)(1),
(2) Date: Nov. 3, 2022

(87) PCT Pub. No.: WO2021/231373
PCT Pub. Date: Nov. 18, 2021

(65) Prior Publication Data
US 2023/0157773 A1    May 25, 2023

Related U.S. Application Data

(60) Provisional application No. 63/022,731, filed on May 11, 2020.

(51) Int. Cl.
*A61B 34/00* (2016.01)
*A61B 17/14* (2006.01)
(Continued)

(52) U.S. Cl.
CPC .............. *A61B 34/30* (2016.02); *A61B 17/14* (2013.01); *A61B 34/10* (2016.02); *A61B 2034/104* (2016.02); *A61B 2034/107* (2016.02)

(58) Field of Classification Search
None
See application file for complete search history.

(56) References Cited

U.S. PATENT DOCUMENTS 9,770,300 B2 * 9/2017 Kwon ................... B25J 3/04
2011/0060345 A1 * 3/2011 Lee .................... A61B 34/30
606/130
(Continued)

FOREIGN PATENT DOCUMENTS

| EP | 3510927 A1 | 7/2019 |
| WO | 2012136223 A1 | 10/2012 |
| WO | 2019032828 A2 | 2/2019 |

OTHER PUBLICATIONS

Int'l Search Report for PCT/US2021/031703, dated Aug. 26, 2021.

*Primary Examiner* — Truc M Do
(74) *Attorney, Agent, or Firm* — Bridgeway IP Law Group, PLLC; Jihun Kim

(57) ABSTRACT

A surgical system is provided for robotically resecting tissue. The system includes a surgical robot with an end-effector configured to remove tissue along a path up to a planned boundary. A computing system interfaces with the surgical robot and includes one or more processors, non-transient storage memory, and software executable instructions. The computing system records deviations between the end-effector and the planned boundary while the end-effector removes tissue along the path during a first pass. The system then determines if the end-effector should perform a subsequent pass along at least a portion of the path based on the recorded deviations. A method for robotically resecting tissue along a path up to a planned boundary is also provided that determined on the recorded deviations, if the end-effector should perform a subsequent pass along at least a portion of the path.

14 Claims, 6 Drawing Sheets

(51) Int. Cl.
   *A61B 34/10*   (2016.01)
   *A61B 34/30*   (2016.01)

(56) References Cited

U.S. PATENT DOCUMENTS

| | | | |
|---|---|---|---|
| 2012/0143084 A1 | 6/2012 | Shoham | |
| 2015/0297177 A1* | 10/2015 | Boctor | A61B 34/30 901/47 |
| 2017/0239006 A1* | 8/2017 | Crawford | A61M 5/172 |
| 2018/0064499 A1* | 3/2018 | Itkowitz | B25J 9/1682 |
| 2019/0365481 A1* | 12/2019 | Otto | A61B 34/25 |
| 2021/0059777 A1* | 3/2021 | Overmyer | A61B 34/71 |

* cited by examiner

MEASUREMENT GUIDED RESURFACING DURING ROBOTIC RESECTION

RELATED APPLICATIONS

This application claims priority benefit of U.S. Provisional Application Ser. No. 63/022,731 filed 11 May 2020; the contents of which are hereby incorporated by reference.

TECHNICAL FIELD

The present invention generally relates to robotic systems, and more particularly to a robotic surgical system that resects tissue along a path up to a boundary and determines if a subsequent pass along at least a portion of the path is required to improve the accuracy of the resection.

BACKGROUND

Throughout a lifetime, bones and joints become damaged and worn through normal use, disease, and traumatic events. Arthritis is a leading cause of joint damage that over time leads to cartilage degradation, pain, stiffness, and bone loss. Arthritis can also cause the muscles articulating the joints to lose strength and become painful.

If the pain associated with the dysfunctional joint is not alleviated by less-invasive therapies, a joint arthroplasty procedure is considered as a treatment. Joint arthroplasty is an orthopedic procedure in which an arthritic or dysfunctional joint surface is replaced with an orthopedic prosthesis.

The accurate placement and alignment of an implant is a large factor in determining the success of joint arthroplasty. A slight misalignment may result in poor wear characteristics, reduced functionality, poor clinical outcomes, and decreased prosthetic longevity.

Computer-assisted orthopedic surgery is an expanding field having applications in total joint arthroplasty (TJA), bone fracture repair, maxillofacial reconstruction, and spinal reconstruction. Robotic surgical systems are particularly useful for surgical procedures requiring dexterity, precision, and accuracy, and generally include some type of pre-operative planning software and a surgical robot. For example, the ROBODOC® surgical system (THINK Surgical, Inc., Fremont, CA) as shown in FIG. 1 aids in the planning and execution of total joint arthroplasty procedures illustratively including total hip arthroplasty (THA) and total knee arthroplasty (TKA). The ROBODOC® pre-operative planning software permits a user to pre-operatively plan the position and orientation of a chosen bone implant (e.g., hip or knee implants) relative to three-dimensional (3-D) bone models of the patient. In the operating room, the surgical plan is transferred to the ROBODOC® surgical robot 100 to precisely mill the bone to receive the implant as planned by the surgeon. The surgical robot 100 generally includes a base 102, a manipulator arm 104 attached to the base, and an end-effector 106 which is actuated or controlled by the manipulator arm 104 as instructed by the surgical plan. The manipulator arm 104 includes various links, joints, and sensors (e.g., encoders) to accurately actuate the end-effector 106, where the sensors can further provide feedback as to the exact position of the end-effector 106 in space. The end-effector 106 may be, for example, a tool having a tool tip, such as a burr or end mill cutter. The surgical robot 100 may further include a digitizer 110 for registering the bone, a monitor 112 to display a graphical user interface to provide workflow instructions to the user, as well as input mechanisms (not shown) for the user to interact with surgical robot 100.

The surgical plan may have instructions for the surgical robot 100 in the form of a cut-file. The cut-file contains instructions (e.g., cut paths, orientations, velocities, feed rates, spindle speeds, etc.) that direct the end-effector 106 to cut the bone according the plan. In the operating room, the bone is first either: a) fixed in position relative to the surgical robot 100 using fixation hardware; or b) a tracking reference marker (e.g., a tracking array) is fixed to the bone to permit a tracking system to track the bone during the procedure. Next, the surgical plan is registered to the bone (typically by way of a 3-D model of the bone) relative to the surgical robot 100 using techniques well known in the art. This provides the position and orientation (POSE) information as to where the surgical robot 100 needs to mill. Subsequently, the surgical robot 100 autonomously (or automatically) executes the cut-file, controlling the end-effector 106 along the various cut paths to form the cavities or surfaces that receive the implant.

Overall, the resulting surfaces and cavities formed by the surgical robot 100 are quite accurate relative to the plan. However, small deviations from the plan are expected while resecting tissue relative to a pre-selected path. Any real-world surgical procedure with a predefined plan, whether manual or robotically automated features such deviations. As long as deviations are kept within the bounds of what is considered clinically acceptable, the procedure can be considered successful. These small deviations are shown in stylized FIG. 2, which depicts the end-effector 106 resecting a tissue such as bone along a pre-planned path in the direction of the arrow 112. It should be appreciated that the relative scale of features is modified for visual clarity. The end-effector 106 is instructed to cut along the path up to an ideal boundary 114, as illustrated by the dotted line. The solid line behind the end-effector 106 illustrates a cut surface 116 that might be formed with the end-effector 106, while un-cut bone 118 is shown in front of the end-effector 106. As shown, the cut surface 116 has slight deviations from the ideal boundary 114.

Because the surgical robot 100 has precise continuous feedback from the sensors in the manipulator arm, a tracking system tracking the end-effector 106, or both as to the end-effector position, the surgical robot 100 is aware of deviations in the cut trajectory, as shown in exemplary FIG. 2. At every point along the path, the deviation can be described as a translation and rotation in 3-D space from the ideal POSE of the end-effector, where the ideal POSE is one that accurately cuts to or along the boundary. The deviation can also be quantified in terms of being with the boundary (tangential to the surface), or out of the surface (normal to the surface). Generally, only the deviations that are out of the surface plane are relevant to the end result of the cutting.

For a robotic surgical system, trajectory deviations are introduced by factors that might include robot actuation biases and vibration, movement of the target anatomy, or unexpected forces imparted by the anatomy. All of these deviation sources are significantly reduced by applying a compensating motion in real-time of the end-effector based on sensor feedback, yet cannot be entirely eliminated. In general, the larger the cutting forces being imparted to the tissue, the more the anatomy moves thereby enhancing deviations. The deviations are also expected to increase with the translational speed of the end-effector. Higher translational speed gives the system less-time to correct actuation biases and also increase cutting forces that may tend to move anatomy. While slow speed of the end-effector limits this contribution to deviation, longer surgical times result, which in turn may introduce clinical complications. Therefore an inherent tradeoff exists between translation cutting speed, equating to the duration of the procedure, and accuracy, equating to implant fit.

Thus, there exists a need for a robotic system and method for resecting a surface up to an ideal or planned boundary with minimal deviation. There is a further need to consider additional trade-offs, such as the time required to complete a surgical procedure, in attempting to minimize such deviations.

SUMMARY OF THE INVENTION

A surgical system is provided for robotically resecting tissue. The system includes a surgical robot with an end-effector configured to remove tissue along a path up to a planned boundary. A computing system interfaces with the surgical robot and includes one or more processors, non-transient storage memory, and software executable instructions. The computing system records deviations between the end-effector and the planned boundary while the end-effector removes tissue along the path during a first pass. The system then determines if the end-effector should perform a subsequent pass along at least a portion of the path based on the recorded deviations.

A method for robotically resecting tissue along a path up to a planned boundary is also provided that includes deviations between the end-effector and the planned boundary being recorded while the end-effector removes tissue along the path during a first pass. Based on the recorded deviations, it is determined if the end-effector should perform a subsequent pass along at least a portion of the path.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

DETAILED DESCRIPTION

Figure 1:
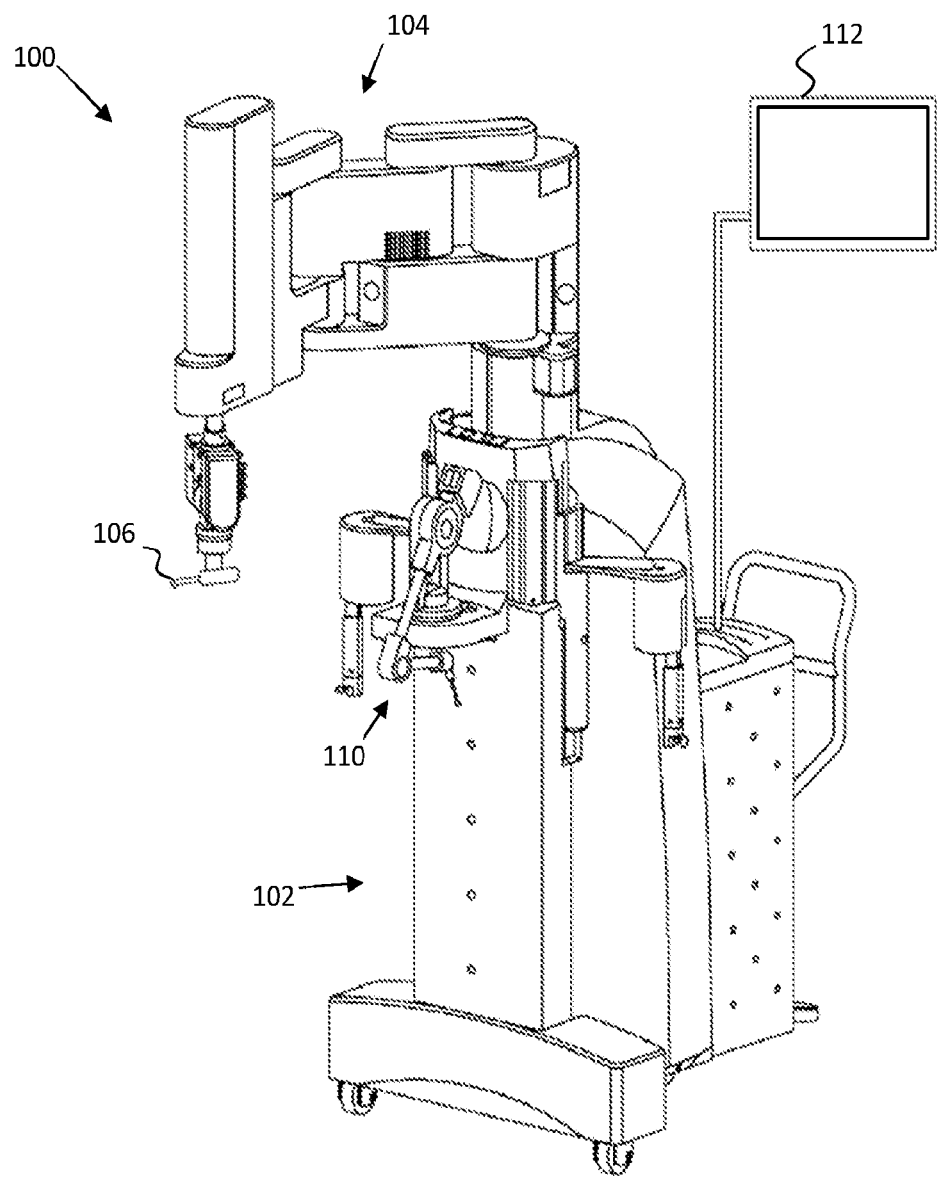
FIG. 1 is a perspective view of a prior art surgical robot.
Figure 2:
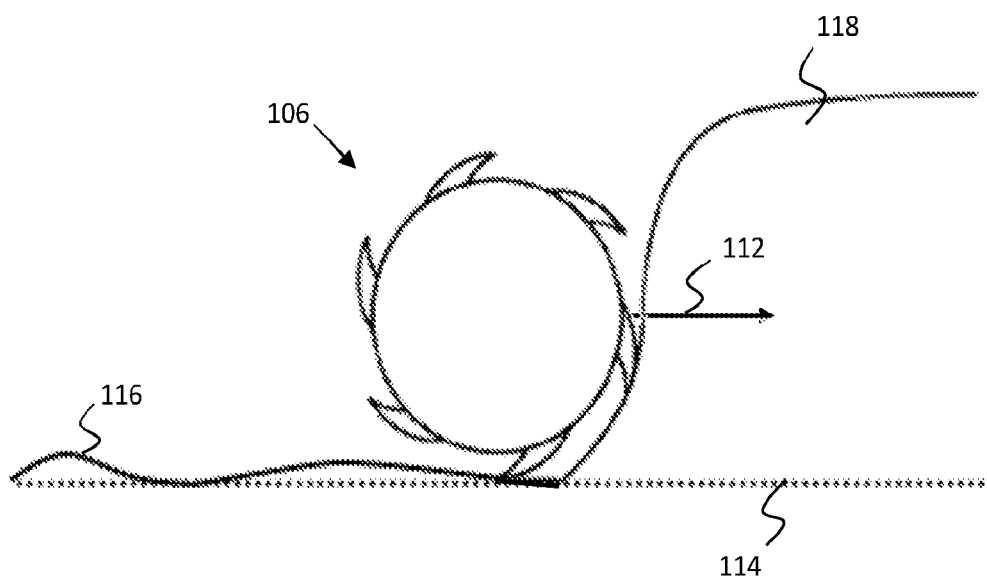
FIG. 2 is a schematic that depicts the prior art action of a tool tip resecting a bone along a pre-planned path in the direction of the arrow up to an ideal boundary (as illustrated by the dotted line), and a solid line behind the tool-tip illustrates an actual surface that has slight deviations from the ideal boundary with relative dimensions being scaled for visual clarity.

The present invention has utility as a system and method for robotically resecting tissue up to a planned boundary with limited deviation, while further taking into consideration trade-offs of the overall surgical time to complete a surgical procedure. Some embodiments of the present invention provide a user with controls to allow for user selection of the relative balance between more accurate resection and longer surgical time to tailor each surgical procedure. The present invention is described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

All publications, patent applications, patents and other references mentioned herein are incorporated by reference in their entirety.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

As used herein, the term "pre-procedure data" refers to data used to plan a medical procedure prior to making modifications to tissue. The pre-procedure data may include one or more of the following: an image data set of tissue (e.g., an image data set acquired via computed tomography (CT), magnetic resonance imaging (MRI), ultrasound, x-ray, laser scan, etc.), a virtual generic model of the tissue, a physical model of the tissue, a virtual patient-specific model of the tissue generated from an image data set of the tissue, a set of data collected directly on the tissue intra-operatively (commonly used with imageless computer-assist devices), etc. As used herein, the term "pre-operative bone data" refers to pre-procedure data involving a bone.

As used herein, the term "digitizer" refers to a device capable of measuring, collecting, recording, and/or designating the location of physical locations (e.g., points, lines, planes, boundaries, etc.) or tissue structures in three-dimensional space. By way of example but not limitation, the "digitizer" may be: a "mechanical digitizer" having passive links and joints, such as the high-resolution electro-mechanical sensor arm described in U.S. Pat. No. 6,033,415 (which U.S. patent is hereby incorporated herein by reference); a non-mechanically tracked digitizer probe (e.g., optically tracked, electromagnetically tracked, acoustically tracked, and equivalents thereof) as described for example in U.S. Pat. No. 7,043,961 (which U.S. patent is hereby incorporated herein by reference); an end-effector of a robotic device; or a laser scanner.

As used herein, the term "digitizing" refers to the collecting, measuring, designating, and/or recording of physical locations or tissue structures in space with a digitizer.

Also described herein are "robotic surgical systems." A robotic surgical system refers to any system requiring a robot controlled by a computer to aid in a surgical procedure. Examples of a robot surgical system include 1-N degree of freedom hand-held surgical system, autonomous or semi-autonomous serial-chain manipulator systems, haptic serial chain manipulator systems, parallel robotic systems, or master-slave robotic systems, as described in U.S. Pat. Nos. 5,086,401; 7,206,626; 8,876,830; 8,961,536; and 9,707,043; and the robotic surgical system described in U.S. Pat. App. Pub. US2020/0367980. In particular inventive embodiments, the surgical system is a robotic surgical system as described below. The surgical system may provide automatic, semi-automatic, power, or haptic control, and any combination thereof.

As used herein, an "end-effector" is a device or tool that interacts with the target object or material (e.g., tissue). Examples of an end-effector include, but not limited to, a burr, end-mill, reamer, drill bit, pin, screw, cutter, saw, laser, and a water-jet.

Also, referenced herein is a surgical plan. For context, a surgical plan is created, either pre-operatively or intra-operatively, by a user using planning software. The planning software may be used to plan one or more resections to be made on the tissue. For example, the planning software may be used to plan the position for an implant relative to pre-operative bone data. The planning software may be used to generate three-dimensional (3-D) models of the tissue (e.g., a patient's bony anatomy) from a computed tomography (CT), magnetic resonance imaging (MRI), x-ray, ultrasound image data set, or from a set of points collected on the tissue intra-operatively. A set of 3-D models (e.g., computer aided design (CAD) models) of the manufacturer's implants are pre-loaded in the software that allows the user to place the components of a desired implant relative to the tissue to designate the best fit, position, and orientation of the implant to the tissue.

As used herein, the term "real-time" refers to the processing of input data within fractions of a millisecond to hundreds of milliseconds such that calculated values are available within 2 seconds of computational initiation.

As used herein, a "cut-file" refers to a software file having set of instructions to automatically or haptically control a surgical robot. The set of instructions illustratively include cut paths, points, virtual boundaries, velocities, accelerations, spindle speeds, feed rates, and any combination thereof to automatically or haptically control the robot relative to target tissue. One or more cut-files may be generated based on the geometry of the implant, the geometry of the tissue models, a planned position of the implant models relative to the tissue models, or a combination thereof using computer-aided manufacturing (CAM) techniques.

As used herein, the term "registration" refers to: the determination of the spatial relationship between two or more objects; the determining of a coordinate transformation between two or more coordinate systems associated with those objects; and/or the mapping of an object onto another object. Examples of objects routinely registered in an operating room (OR) illustratively include: computer-assisted systems/devices; anatomy (e.g., bone); pre-procedure data (e.g., 3-D virtual bone models); medical planning data (e.g., an implant model positioned relative to pre-operative bone data, a cut-file defined relative to an implant model and/or pre-operative bone data, virtual boundaries defined relative to an implant model and/or pre-operative bone data, virtual planes defined relative to an implant model and/or pre-operative bone data, or other cutting parameters associated with or defined relative to an implant model and/or the pre-operative bone data); and any external landmarks (e.g., a tracking array affixed to a bone, an anatomical landmark, a designated point/feature on a bone, etc.) associated with the tissue (if such landmarks exist). Methods of registration known in the art are described in U.S. Pat. Nos. 6,033,415; 8,010,177; 8,036,441; and 8,287,522; and U.S. Patent Application Publication 2016/0338776, which patents and publications are hereby incorporated herein by reference. In particular embodiments with orthopedic procedures, the registration procedure relies on the manual collection of several points (i.e., point-to-point, point-to-surface) on the bone using a tracked digitizer where the surgeon is prompted to collect several points on the bone that are readily mapped to corresponding points or surfaces on a representation of the bone (e.g., a 3-D bone model). The points collected from the surface of a bone with the digitizer may be matched using iterative closest point (ICP) algorithms to generate a transformation matrix. The transformation matrix provides the correspondence between the position of the bone in an operating room (OR) with the bone model to permit the surgical device to execute the plan.

Also used herein is the term "optical communication" which refers to wireless data transfer via infrared or visible light that are described in U.S. Pat. No. 10,507,063 and assigned to the assignee of the present application.

Embodiments of the present invention provide for an improved robotic system that resects tissue up to a pre-planned or ideal boundary with minimal deviation. In a robotic surgical procedure, small deviations may occur between the resulting resection relative to an ideal boundary due to vibrations of the manipulator arm, movement of the anatomy, and unexpected forces imparted by the anatomy. While the deviations are small, it may be desirable to have a more accurate resection especially in the context of surgical procedures. One particular application requiring such accuracy is joint arthroplasty where the bone is resected up to a boundary to receive an implant as planned by the user. While the present invention is further detailed with respect to orthopedic procedures in the accompanying drawings, it is to be understood that the present invention is applicable to robotic procedures in general and regardless of anatomy, as well as non-surgical applications where a precise and accurate resection is required on an object. By way of example but not limitation, the system and method of the present invention may be applicable to medical procedures performed on: a) hard tissues (e.g., bones, teeth) including bones in the hip, ankle, shoulder, spine, jaw, skull, elbow, wrist, hands, fingers, feet, toes, etc., as well as revision of initial repair or replacement of any joints or bones; and b) soft tissues (e.g., organs, muscles, connective tissue) including the brain, ligaments, tendons, lungs, heart, skin, etc.

In a specific inventive embodiment, a method is provided that calculates the deviations between a resected surface relative to an ideal boundary and determines whether to resurface a region of tissue if the deviations exceeds predefined criteria. The resection may be modeled as cutting tissue up to a 3-D boundary. It is assumed that tissue can be removed within a certain region up to the boundary with no deleterious effects. The boundary may be a concave enclosed space, in the case of removing a tumor or organ with a robotic controlled laparoscopic tool, or alternatively, the boundary may be a generally planar or convex surface in the case of an implant site for total knee arthroplasty. The robotic system records the position and orientation (POSE) deviations of the end-effector at every point from the boundary while resecting the tissue, and computes cumulative statistics for regions of resected tissue. The statistics might include the maximum, mean, and standard deviation of translational and angular deviation for that tissue region. The computation of robotic end-effector deviations are described in detail below. An example of computing robotic end-effector deviation for the purposes of calibration is described in J. L. Caenen et al., Identification of geometric and non-geometric parameters of robots, *IEEE International Conference on Robotics and Automation* 2 (1990) 1032-1037; K. Schroer, et al., Modeling closed-loop mechanisms in robots for purposes of calibration, *IEEE Transactions on Robotics and Automation* 13 (1997) 218-229. The boundaries of the regions of resected tissue for the purposes of computing the cumulative statistics and deviation analyses may be somewhat arbitrary. The regions should be large enough such that meaningful statistical parameters can be estimated over the POSE deviation samples within the region, while still remaining spatially localized. If after cutting one or more regions, the robotic system determines that the deviation is higher than desired for a given tissue region being cut, the surgical robot revisits that region in a second (or subsequent) pass, cutting the surface again. The second pass may be performed in a manner such that the deviations are statistically uncorrelated with the deviations of the first pass, and possibly with different operating conditions, such as a lower speed, to reduce the deviations. The system does not need to revisit all regions of the surface in some inventive embodiments and instead only those with the highest recorded deviations. As a result, there is only a nominal increase in the total time of the surgery. In addition, the user may have the option to re-visit one or more regions at their discretion in the interest of other factors such as the surgical time.

Figure 3:
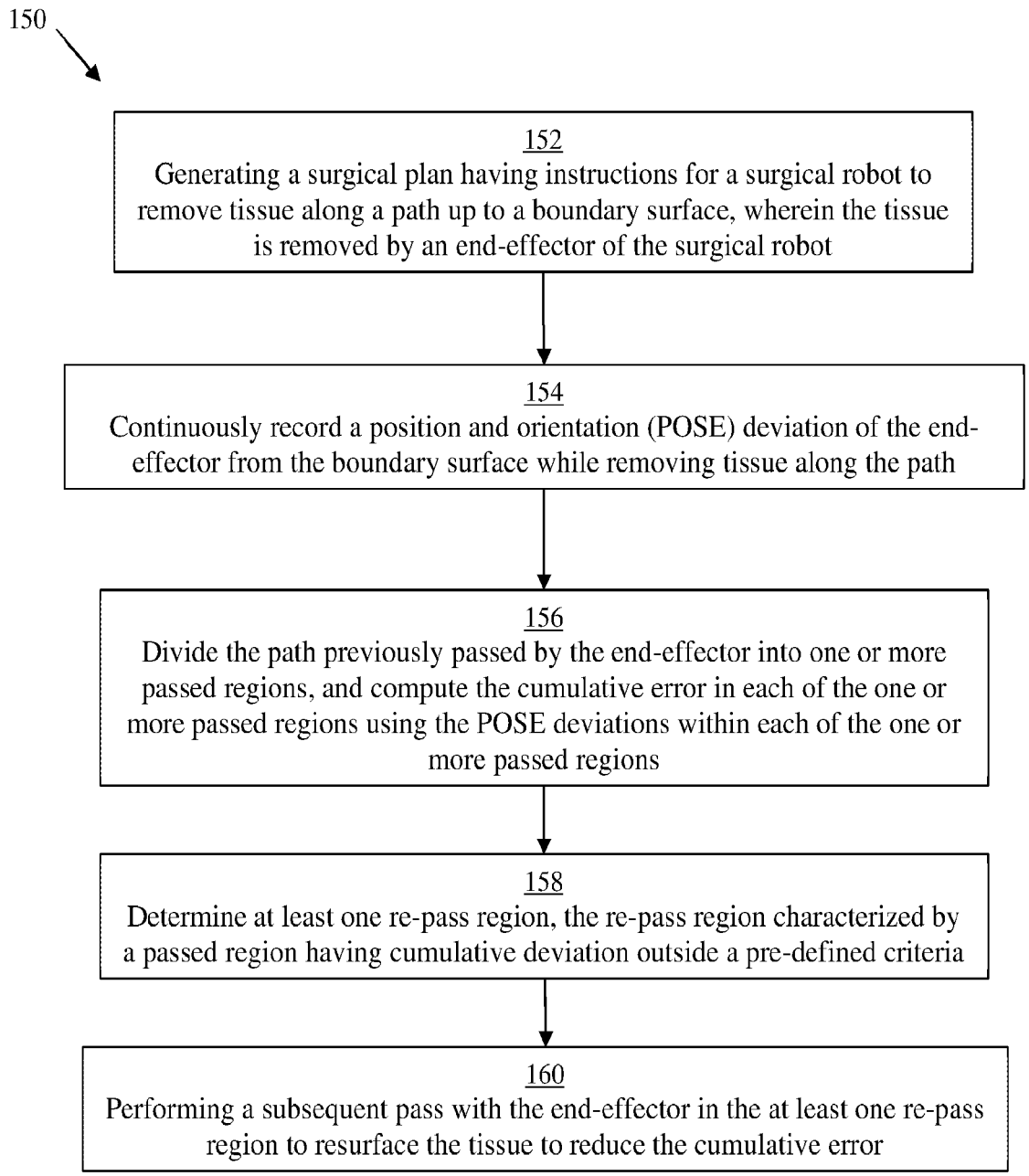
FIG. 3 depicts a flow diagram of a method that determines one or more regions of resected tissue to be resurfaced to better match with an ideal or planned boundary in accordance with embodiments of the invention.

With reference now to the figures, FIG. 3 depicts a flow diagram of an embodiment of an inventive method 150 that determines one or more regions of resected tissue to be resurfaced to better match with an ideal or planned boundary. The method 150, in some embodiments, begins by generating a surgical plan having instructions for a surgical robot to remove tissue along a path up to a boundary, where the tissue is removed by an end-effector of a surgical robot (Block 152). In the operating room, a tracking reference marker (e.g., tracking array) is fixedly attached to the tissue to permit a tracking system to track the tissue. The surgical plan is then registered to the tissue such that the surgical robot knows the POSE of the tissue to be resected as defined in the surgical plan. As the surgical robot resects tissue along one or more paths, the POSE deviations between the end-effector and the boundary is continuously monitored and recorded (Block 154). The path(s) previously passed by the end-effector is then divided into one or more "passed" regions, where the cumulative deviation in each of the one or more passed regions is calculated using the POSE deviations within each of the one or more passed regions (Block 156). It is appreciated that in some inventive embodiments, a weighting function is readily applied to deviations in a particular portion of a given cut path in response to a need for greater accuracy and precision in a given region. A re-pass region may then be determined, where a re-pass region is a passed region having cumulative deviation outside predefined criteria (Block 158). A subsequent pass with the end-effector may be performed in the re-pass region to resurface the tissue to reduce the cumulative deviation (Block 160). One or more re-pass regions may be resurfaced as desired by the user or may be automatically performed by the surgical robot. Specific embodiments of the method 150 for joint replacements procedures is described below.

A surgical plan may be generated in a pre-operative planning software program using pre-operative bone data and one or more CAD models of an implant. A user may position one or more implant models relative to the pre-operative bone data (e.g., 3-D models of the patient's bones) to designate the best fit, fill, and/or alignment for the implant with the patient's bone. A cut-file may be associated or tied with each implant model and size such that the cutting instructions (e.g., cut paths, boundaries) in the cut-file are likewise positioned relative to the pre-operative bone data based on the designated position of the implant model. The surgical plan is then saved and transferred to the surgical robot. The final surgical plan may include the pre-operative bone data and the cut-file, which is then transferred to the surgical robot in the operating room (OR). In other inventive embodiments, a surgical plan may be generated in the OR, where a model of the bone is generated by collecting a plurality of points on the surface of the exposed bone. An implant model is then positioned relative to the intra-operatively generated bone model, where one or more cut-files are associated with the implant models. In this case, the surgical plan may already be uploaded to the surgical robot.

It should be appreciated, that the cut-file and/or cutting instructions may be defined based on: a) the geometry of the implant model; b) the pre-operative bone data (e.g., the outline of the edges of the cortical bone relative to the less dense trabecular or intramedullary space on a CT scan); or c) the position of an implant model relative to the pre-operative bone data (e.g., the intersection of an implant model with a bone model). Other cutting instructions for a surgical robot may be generated for the same or other applications using CAM techniques known in the art.

In the operating room, the bone is exposed and a tracking reference marker, such as a tracking array, is fixedly attached to the bone to permit the tracking system to track the bone in real-time. The surgical plan is then registered to the bone in the coordinate frame of the tracking reference marker using registration techniques known in the art. This permits the tracking system to update/track the POSE of the cutting instructions (including the POSE of the planned boundaries) as the bone moves by way of the tracking reference marker. A tracking reference marker may also be fixedly attached to the surgical robot or end-effector to permit the tracking system to track the POSE of the end-effector of the surgical robot in real-time. The surgical system now knows the coordinates of the cutting instructions registered to the tissue and the coordinates of the end-effector such that the end-effector can accurately execute the cutting instructions on the tissue in the planned location. In addition, the coordinates of the cutting instructions and/or the coordinates of the end-effector can be monitored and updated in real-time as the end-effector and/or bone move during the surgical procedure.

As the surgical robot resects the bone along one or more paths, the POSE deviations between the end-effector position and the panned boundary is monitored and recorded in real-time. The POSE deviations may be calculated by several different methods. A particular embodiment of a method to calculate the POSE deviations utilizes the tracked POSE of the cutting instructions relative to the tracked POSE of the end-effector. The tracking system knows the real-time POSE of the planned boundaries based on: a) the POSE of the tracking reference marker fixed to the bone; and b) the registration of the cutting instructions (having the planned boundaries) to the bone. The tracking system knows the real-time POSE of the end-effector based on: a) the POSE of the tracking reference marker fixed to the robot; and b) either: i) a calibrated relationship between the tracking reference marker fixed to the end-effector; or ii) the robot joint sensor feedback (i.e., joint encoders) and the kinematics of the robotic arm (e.g., Denavit-Hartenberg parameters) relative to the position of the tracking reference marker fixed to the robot. The difference between the real-time POSE of the planned boundary and the real-time POSE of the end-effector is the calculated POSE deviation. The POSE deviation may be calculated and recorded at each point along the resection surface, at specified time intervals (e.g., every millisecond), or at a specified translational distance interval (e.g., every millimeter). Another particular embodiment of a method to calculate the POSE deviations utilizes the real-time POSE of the end-effector alone. The surgical robot knows the ideal trajectory for the end-effector to resect tissue up to the planned boundary(s) based on the POSE of the cutting instructions registered to the bone. Based on the kinematic model of the robot and the feedback from the joint sensors in the robot arm, the surgical robot can continuously calculate the forward kinematics of the surgical robot and therefore the real-time POSE of the end-effector. Any actuation biases, vibrations, or chatter sensed by the joint sensors that deviate from the ideal trajectory is recorded as a POSE deviation. These POSE deviations may likewise be monitored and recorded at each point along the resection surface, at specified time intervals (e.g., every millisecond), or at a specified translational distance interval (e.g., every millimeter).

Figure 4:
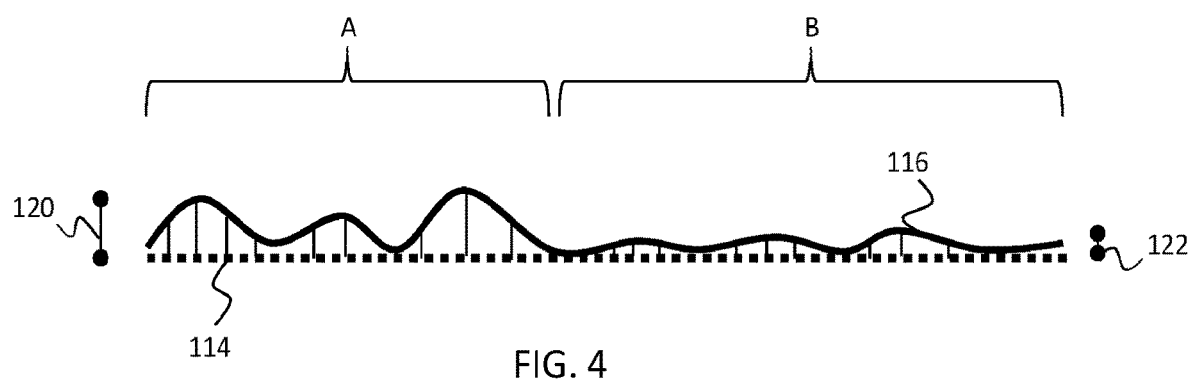
FIG. 4 is a schematic diagram that shows an ideal boundary relative to an actual resected surface where position and orientation (POSE) deviations are represented as lines spanning between the ideal boundary and the resected surface, where after resecting a portion of the bone, the robotic system divides the resected surface into one or more "passed" regions shown as region 'A' and a second passed region 'B' in accordance with embodiments of the invention with relative dimensions being scaled for visual clarity.

With reference to FIG. 4, a planned boundary 114 is shown relative to a resected surface 116 formed by an end-effector. The POSE deviations are illustratively represented as the lines spanning between the planned boundary 114 and the resected surface 116. After resecting some of the bone, the robotic system (e.g., a computer of the robotic system) divides the resected surface into one or more "passed" regions. FIG. 4 depicts a first passed region 'A' and a second passed region 'B'. The resected tissue may be divided in real-time, after one or more paths are completed, after a certain amount of tissue has been resected, after a certain amount of resection time, or a combination thereof. The boundaries of the passed regions (e.g., where passed region A ends and passed region B begins) may be arbitrary, but should be large enough such that meaningful statistical parameters may be computed over the POSE deviation samples within that region, while still remaining spatially localized. In some inventive embodiments, the boundaries that define a passed region ranges from 5 millimeters (mm) in length to 100 mm in length, but may vary depending on the application. Statistics are computed for each passed region. The statistics illustratively include the maximum, mean, and standard deviation of translational and angular deviation for a passed region. In FIG. 4 the computed cumulative deviation for region A is illustratively represented by the bounded line 120, and the computed cumulative deviation for region B is illustratively represented as the bounded line 122. The robotic system may determine that region A has a cumulative deviation outside predefined criteria (e.g., the max error, mean error, or standard deviation is greater than a desired threshold) and is labelled as a potential re-pass region, while region B is within the predefined criteria. The robotic system may then instruct the end-effector to perform a subsequent pass with the end-effector in region A to reduce the cumulative deviation. In particular embodiments, the subsequent pass (or re-pass) is performed in a manner such that the deviations are statistically uncorrelated with the deviations of the first pass, and possible with different operating conditions, such as lower translational speed, to reduce deviation. If the robotic system identifies multiple re-pass regions where the cumulative deviation exceeds the predefined criteria, the system may not need to revisit all these re-pass regions, only those regions with a cumulative deviation that exceed an even higher threshold, so there is only a nominal increase in the total time of the surgery. For example, if ten re-pass regions are identified, the system or a user may decide to resurface only five of the ten re-pass regions, where those five re-pass regions have the highest cumulative deviation. It is appreciated that the threshold can be preselected or based on evaluation during a procedure. Likewise, a threshold number of re-pass regions permissible for resurfacing may be preselected or based on evaluation during a procedure.

The deviation for each re-pass region is readily modelled as an independent Gaussian distributed random process to predict the net deviation probability distribution function (PDF) for two successive passes. The PDF is succinctly summarized in S. Nadarajah et al, "Exact Distribution of the Max/Min of Two Gaussian Random Variables", *IEEE Transactions on Very Large Scale Integration (VLSI)Systems*, Vol. 16, No. 2, (2008) 210-212, based on the derivation in A. P. Basu et al., "Identifiability of the multinormal and other distributions under competing risks model," *J. Multivariate Anal.*, vol. 8, (1978) 413-429. Note that even if the mean deviation for any pass is zero (implying no bias), the net mean of multiple passes over the surface is not zero because each resection can only exceed the depth of the previous resection. That is, the boundary can be considered the minimum or maximum of two independent random processes. This implies it is necessary to intentionally offset one or both of the passes away from the desired surface so as the net expected mean is near zero for their cumulative statistics. The same concept can be extrapolated to more than two passes.

Figure 5:
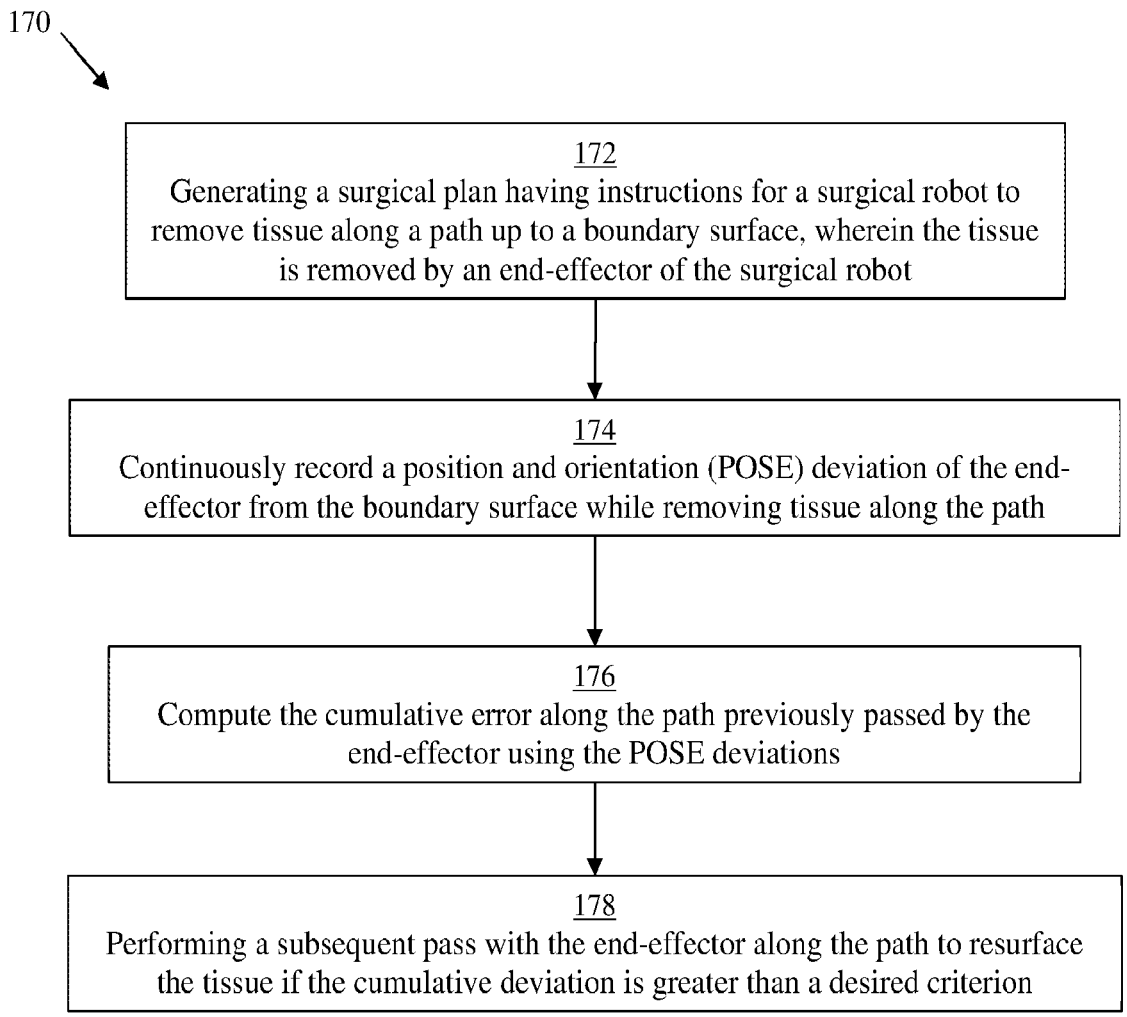
FIG. 5 is a flow diagram of a method that computes the cumulative deviation along the length of an entire path, or cut-file, to determine if a subsequent pass of an end-effector along the entire length of the path is required to resurface tissue to better match with an ideal or planned boundary in accordance with embodiments of the invention.

FIG. 5 is a flow diagram of an embodiment of an inventive method 170 that computes the cumulative deviation along the length of an entire path, or cut-file, to determine if a subsequent pass of the end-effector along the entire length of the path is required to resurface the tissue to better match with an ideal or planned boundary. The method 170, in some embodiments, begins by generating a surgical plan having instructions for a surgical robot to remove tissue along a path up to a boundary, where the tissue is removed by an end-effector of a surgical robot (Block 172). In the operating room, a tracking reference marker (e.g., tracking array) is fixedly attached to the tissue to permit a tracking system to track the tissue. The surgical plan is then registered to the tissue such that the surgical robot knows the POSE of the tissue to be resected as defined in the surgical plan. As the surgical robot resects tissue along one or more paths, the POSE deviations of the end-effector from the boundary is continuously monitored and recorded (Block 174). The cumulative deviation along the path previously passed by the end-effector is computed using the POSE deviations (Block 176). A subsequent pass with the end-effector may be performed along the path to resurface the tissue to reduce the cumulative deviation (Block 178). The method 170 may be beneficial when there are multiple cut-files, or a cut-file already contains a plurality of cut paths with each path having a predefined start and end. The robotic system can then decide if one or more cut paths from the plurality of cut paths needs to be resurfaced. Therefore, the robotic system does not need to necessarily divide the resected tissue into "passed" regions as described in the aforementioned method 150 of FIG. 3.

Specific Characteristics for Total Knee Arthroplasty

In the case of cutting resection planes for a total knee arthroplasty procedure, the first contact of the end-effector with the hard cortical bone surface results in the highest forces exerted on the bone during the procedure, the highest potential movement of the bone, and in turn the highest for potential deviation. After the first pass to form a planar resection, re-passing parts of the same path with the end-effector results in much lower forces, and thus much lower deviation. It is appreciated that this is true for an end-effector with the same rotation speed and that forces will change in predictable ways if the end-effector speed is changed relative to the first pass. While lower speed is typically desirable when the cumulative deviation must be reduced substantially, in some instances when only a small amount of material is being removed in a re-pass, high speed operation of the end-effector may be advantageous and quicker. The speed in this context relating to rotary speed, translation speed, or both. If the robotic system records where the maximal deviations are along the resected cut, the surgical robot can re-pass just those positions on the bone as the end-effector moves outward from completing a cut phase. A cut phase refers to a "phase" in the cutting instructions, where each phase contains instructions for the surgical robot to be executed in a particular order. For example, a cut-file may be separated into a first cut phase, a second cut phase, and a third cut phase, where the first cut phase has instructions for the surgical robot to first cut the lateral side of the distal femur, the second cut phase has instructions for the surgical robot to cut a medial side of the distal femur next, and the third cut phase has instructions for the surgical robot to mill holes in the distal femur to receive the pegs of the femoral knee implant component. A re-orientation of the manipulator arm, pause of the surgical robot, or an end-effector tool change may occur between each phase.

When performing a second or subsequent pass with the end-effector in a re-pass region or along a path, the second or subsequent pass is preferably performed in a manner such that the computed deviations are statistically uncorrelated with the deviations of the first, or previous pass. Experiments have shown that performing a second pass with the end-effector in an opposite direction than the previous direction of motion in the first pass results in deviation that is uncorrelated with the first pass. On additional passes, the target motion of the end-effector is preferably shifted slightly outside of the original surface so as to not introduce a bias yet still reduce the net deviation over the re-pass region. The optimal offset for the second pass is easily determined mathematically based on the statistics computed from the first pass and predictable for the second pass.

User Interface

A key characteristic of the system and methods described herein is that the robotic system is aware of the POSE deviations and cumulative deviation between the resected surface and the ideal boundary. In particular embodiments, the deviations may be displayed in real-time to the user, where the user can set and/or adjust the predefined criteria to a particular threshold deviation that dictates whether the surgical robot should resurface a passed region or cut path. The threshold deviation may have a finite minimum so that the system can actually achieve the desired degree of deviation. The system may then display which passed regions of resected tissue are not meeting the threshold deviation and then perform a subsequent pass in only those regions. After the subsequent pass, the system may display the newly achieved surface profile. The tighter the user sets the threshold deviation, the more regions that will need to be resurfaced, and at slower end-effector speeds, thus increasing the time of the surgical procedure. The additional time to perform the resurfacing may be immediately predicted, where the additional time can be provided to the user as feedback. The user may then decide whether the achieved deviation profile is good enough, or whether to spend additional time with the resurfacing.

Variant Approach with Complete Systematic Resurfacing

In some inventive embodiments, there may be several regions that exceed the predefined criteria for one or more cut paths, one or more surfaces, or the entirety of a cut-file. In these cases, the robotic system may automatically perform two passes with the end-effector over said one or more cut paths, one or more surfaces, or the entirety of the cut-file. This may be efficiently achieved by moving along the cut path in a forward direction, and then upon reaching the last point for a given path, moving the end-effector back along the path in a backwards direction. As mentioned before, the reverse movement has proven to have deviation that is uncorrelated with the forward movement. If this strategy is committed to from the outset, it may be advantageous to apply a small bias away from the target surface for the first pass, and then exactly hit the target surface on the second pass when resistive forces and anatomical motion are much reduced relative to the first pass.

Bone Fixation and Monitoring

In specific inventive embodiment, the aforementioned methods may be applied to a robotic surgical system that relies on bone fixation and bone motion monitoring. The method, in some embodiments, begins by generating a surgical plan having instructions for a surgical robot to remove tissue along a path up to a boundary, where the tissue is removed by an end-effector of a surgical robot. In the operating room, the bone is fixed relative to the surgical robot using fixation hardware. For example, bone fixation may include the use of pins, rods, and clamps, where a pin is inserted into the bone, a first end of a rod is clamped to the pin, and the other end of the rod is fixed to the base of the surgical robot. A bone motion monitor may also be assembled to the bone to monitor motion of the bone during the procedure. The bone motion monitor may include a probe attached to one or more strain gauges. The probe may be pressed against the bone such that the strain gauges can monitor bone motion in 1 to 6 degrees-of-freedom. The surgical plan is then registered to the bone using registration techniques known in the art such that the surgical robot knows the POSE of the bone to be resected as defined in the surgical plan. As the surgical robot resects bone along one or more paths, POSE deviations of the end-effector from a boundary is continuously monitored and recorded. The POSE deviations may be calculated by several different methods. A particular embodiment of a method to calculate the POSE deviation utilizes the POSE of the end-effector and an amount of bone movement detected by the bone motion monitor. The real-time POSE of the end-effector is known based on joint sensor feedback and the kinematic model of the robot as described above. The amount of movement of the bone is detected by the bone motion monitor, and in some embodiments, the amount of movement may not have directionality and only a magnitude. The POSE deviation may then be calculated as the difference between the POSE of the end-effector and the amount of movement detected by the bone motion monitor. These POSE deviations may be monitored and recorded at each point along the resection surface, at specified time intervals (e.g., every millisecond), or at a specified translational distance interval (e.g., every millimeter). Another particular embodiment of a method to calculate the POSE deviation utilizes the real-time POSE of the end-effector alone. The surgical robot knows the ideal trajectory for the end-effector to resect tissue up to the planned boundary(s) based on the POSE of the cutting instructions registered to the bone. Based on the kinematic model of the robot and the feedback from the joint sensors in the robot arm, the surgical robot can continuously calculate the forward kinematics of the surgical robot and therefore the real-time POSE of the end-effector. Any actuation biases, vibrations, or chatter sensed by the joint sensors that deviate from the ideal trajectory is recorded as a POSE deviation. These POSE deviations may likewise be monitored and recorded at each point along the resection surface, at specified time intervals (e.g., every millisecond), or at a specified translational distance interval (e.g., every millimeter).

The path(s) previously passed by the end-effector is then divided into one or more "passed" regions, where the cumulative deviation in each of the one or more passed regions is calculated using the POSE deviations within each of the one or more passed regions. It is appreciated that in some inventive embodiments, a weighting function is readily applied to deviations in a particular portion of a given cut path in response to a need for greater accuracy and precision in a given region. A re-pass region may then be determined, where a re-pass region is a passed region having cumulative deviation outside a predefined criteria. A subsequent pass with the end-effector may be performed in the re-pass region to resurface the tissue to reduce the cumulative deviation. One or more re-pass regions may be resurfaced as desired by the user or may be automatically performed by the surgical robot. Specific embodiments of the method are further described below.

In specific embodiments, it may not be necessary to specifically calculate the POSE deviation between the end-effector and a planned boundary to determine one or more re-pass regions for resurfacing. In this embodiment, an amount of bone movement may be sufficient enough to warrant a subsequent pass to resurface a region of bone. For example, as the end-effector is resecting bone in a particular region, the bone motion monitor may sense an excessive amount of movement or a sustained amount of movement over a certain time frame. A threshold may be set to trigger a start and stop sequence to define an interval for resurfacing. For example, if the bone moves above a threshold, the system begins recording the POSE of the end-effector and continues recording the POSE of the end-effector as it resects tissue until the bone motion falls below the threshold, at which point the recording stops. The bone resected by the end-effector during the recording may define an interval of bone that may need resurfacing (due to the excessive bone motion). The system or a user may then determine if it is necessary to perform a subsequent pass with the end-effector in the interval to resurface the bone.

Robotic Surgical System

Figure 6:
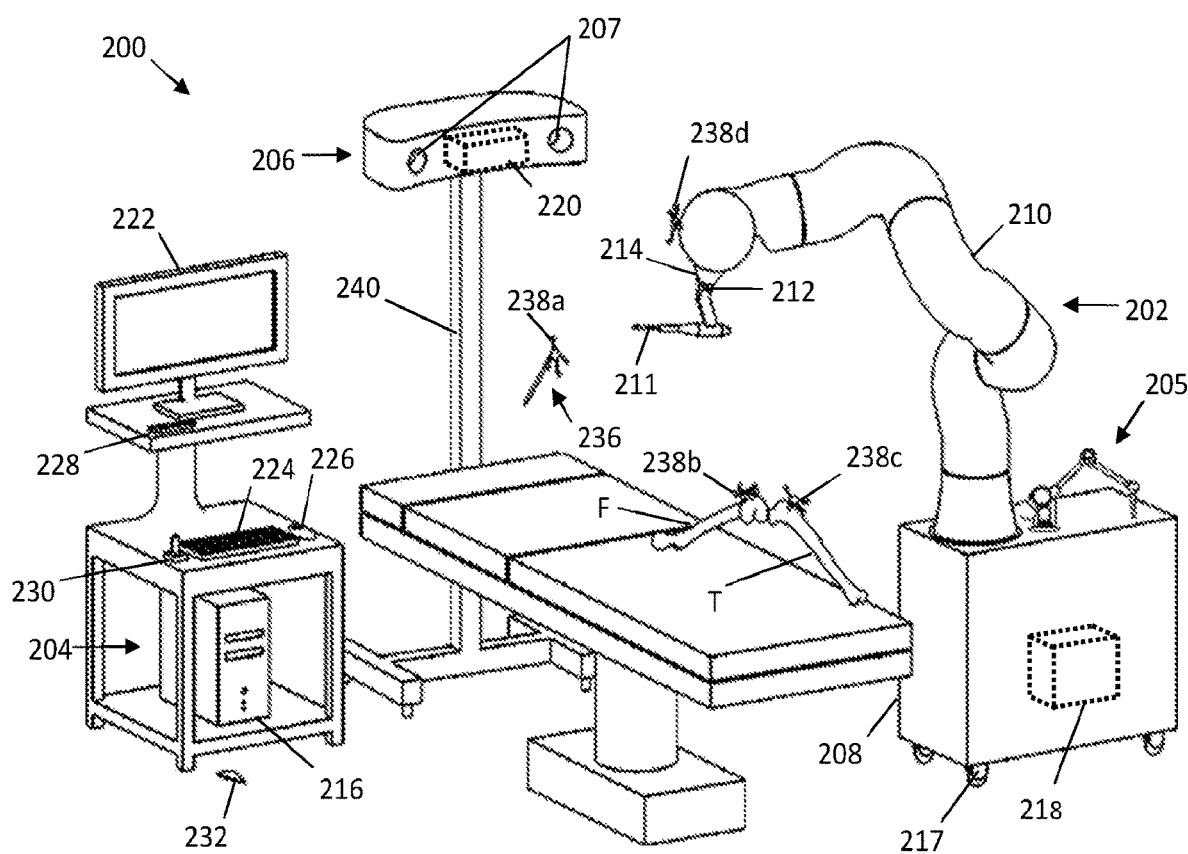
FIG. 6 depicts a prior art surgical system in the context of an operating room (OR) with a robotic surgical device, where the surgical system is capable of performing embodiments of the inventive method for resecting bone surfaces up to a planned or ideal boundary with reduced deviation during a robotic-assisted orthopedic surgery.

FIG. 6 depicts a robotic surgical system 200 in the context of an operating room (OR) to prepare a femoral and tibial bone in a non-limiting example of a total knee arthroplasty using embodiments of the inventive method for resecting bone surfaces up to a planned or ideal boundary with minimal deviation during a robotic-assisted orthopedic surgery. The surgical system 200 includes a surgical robot 202, a computing system 204, and an optional tracking system 206. The surgical robot 202 may include a movable base 208, a manipulator arm 210 connected to the base 208, an end-effector 211 located at a distal end 212 of the manipulator arm 210, and a force sensor 214 positioned proximal to the end-effector 211 for sensing forces experienced on the end-effector 211. The base 208 includes a set of wheels 217 to maneuver the base 208, which may be fixed into position using a braking mechanism such as a hydraulic brake. The base 208 may further include an actuator to adjust the height of the manipulator arm 210. The manipulator arm 210 includes various joints, links, and sensors (e.g., encoders) to accurately manipulate the end-effector 211 in various degrees of freedom. The joints are illustratively prismatic, revolute, spherical, or a combination thereof. The end-effector 211 may be a motor-driven end-mill, cutter, drill-bit, or other bone removal device.

The computing system 204 may generally include a planning computer 216; a device computer 218; a tracking computer 220; and peripheral devices. The planning computer 216, device computer 218, and tracking computer 220 may be separate entities, one-in-the-same, or combinations thereof depending on the surgical system. Further, in some embodiments, a combination of the planning computer 216, the device computer 218, and/or tracking computer 220 are connected via wired or wireless communication. The peripheral devices allow a user to interface with the surgical system components and may include: one or more user-interfaces, such as a display or monitor 222 to display a graphical user interface (GUI); and user-input mechanisms, such as a keyboard 224, mouse 226, pendent 228, joystick 230, foot pedal 232, voice control software (not shown), or the monitor 222 that in some inventive embodiments has touchscreen capabilities.

The planning computer 216 contains hardware (e.g., processors, controllers, and/or memory), software, data and/or utilities that are in some inventive embodiments dedicated to the planning of a surgical procedure, either pre-operatively or intra-operatively. It is appreciated that the planning computer functions may be spread over more than one device, and may be performed all or part in cloud computing environment. This may include reading pre-operative bone data, displaying pre-operative bone data, manipulating pre-operative bone data (e.g., image segmentation), constructing three-dimensional (3D) virtual models, storing computer-aided design (CAD) files, providing various functions or widgets to aid a user in planning the surgical procedure, and generating surgical plan data. The final surgical plan may include pre-operative bone data, patient data, registration data including the position of a set of points P defined relative to the pre-operative bone data for registration, trajectory parameters, and/or a set of instructions to operate the surgical robot 202. The set of instructions may include instructions for the surgical robot to modify a volume of bone to receive an implant. The set of instructions may illustratively be: a cut-file having a set of cutting parameters/instructions (e.g., cut paths, velocities) to automatically modify the volume of bone; a set of virtual boundaries defined to haptically constrain a tool within the defined boundaries to modify the bone; a set of boundaries coupled with power or actuation control of a tracked surgical device to ensure the end-effector only removes bone within the boundaries; a set of planes or drill holes to drill pins or tunnels in the bone; or a graphically navigated set of instructions for modifying the tissue. In particular inventive embodiments, the set of instructions is a cut-file for execution by a surgical robot to automatically modify the volume of bone, which is advantageous from an accuracy and usability perspective. The surgical plan data generated from the planning computer 216 may be transferred to the device computer 218 and/or tracking computer 220 through a wired or wireless connection in the operating room (OR); or transferred via a non-transient data storage medium (e.g., a compact disc (CD), a portable universal serial bus (USB) drive) if the planning computer 216 is located outside the OR.

The device computer 218 in some inventive embodiments is housed in the moveable base 208 and contains hardware, software, data and/or utilities that are preferably dedicated to the operation of the surgical robotic device 202. This may include surgical device control, robotic manipulator control, the processing of kinematic and inverse kinematic data, the execution of registration algorithms, the execution of calibration routines, the execution of the set of instructions (e.g., cut-files, the trajectory parameters), coordinate transformation processing, providing workflow instructions to a user, and utilizing position and orientation (POSE) data from the tracking system 206. It is appreciated that the device computer functions may be spread over more than one device and may be performed all or part on the planning computer or in cloud computing environment. In some embodiments, the surgical system 200 includes a mechanical digitizer arm 205 attached to the base 208. The digitizer arm 205 may have its own tracking computer or may be directly connected with the device computer 218. The mechanical digitizer arm 205 may act as a digitizer probe that is assembled to a distal end of the mechanical digitizer arm 205. In other inventive embodiments, the system includes a tracked hand-held digitizer device 236 with a probe tip.

The tracking system 206 may be an optical tracking system that includes two or more optical detectors 207 (e.g., cameras) to detect the position of fiducial markers (e.g., retroreflective spheres, active light emitting diodes (LEDs)) uniquely arranged on rigid bodies. The fiducial markers arranged on a rigid body are collectively referred to as a tracking array (238a, 238b, 238c, 238d), where each tracking array has a unique arrangement of fiducial markers, or a unique transmitting wavelength/frequency if the markers are active LEDs. The fiducial markers may alternatively be directly incorporated or integrated with the surgical device. An example of an optical tracking system is described in U.S. Pat. No. 6,061,644. The tracking system 206 may be built into a surgical light, located on a boom, a stand 240, or built into the walls or ceilings of the OR. The tracking system computer 220 may include tracking hardware, software, data, and/or utilities to determine the POSE of objects (e.g., bones B, surgical device 202) in a local or global coordinate frame. The POSE of the objects is collectively referred to herein as POSE data, where this POSE data may be communicated to the device computer 218 through a wired or wireless connection. Alternatively, the device computer 218 may determine the POSE data using the position of the fiducial markers detected from the optical receivers 207 directly.

The POSE data is determined using the position data detected from the optical detectors 207 and operations/processes such as image processing, image filtering, triangulation algorithms, geometric relationship processing, registration algorithms, calibration algorithms, and coordinate transformation processing.

The POSE data is used by the computing system 204 during the procedure to update the POSE and/or coordinate transforms of the bone B, the surgical plan, and the surgical robot 202 as the manipulator arm 210 and/or bone(s) (F, T) move during the procedure, such that the surgical robot 202 can accurately execute the surgical plan.

In another inventive embodiment, the surgical system 200 does not include an optical tracking system, but instead employs a mechanical arm 205 that may act as a tracking system 206 as well as a digitizer. If the bone is not tracked, a bone fixation and monitoring system may fix the bone directly to the surgical robot 202 to monitor bone movement as described in U.S. Pat. No. 5,086,401. Furthermore, it should be appreciated that other tracking systems may be employed including electromagnetic, acoustic, and radiofrequency tracking systems.

The device computer 218 and/or tracking computer 220 further includes one or more processors, and non-transient memory having software executable instructions stored therein for performing embodiments of the inventive methods 150 and 170 described herein. More particularly, the software executable instructions when executed by the processor may cause the processor to perform one or more of the following: calculate the transformation to register the surgical plan relative to the bone; continuously calculate, record, and store the POSE deviations of the end-effector 211 from the planned boundary while the end-effector is resecting tissue (as described above); determine if the end-effector should perform a subsequent pass along at least a portion of the path based on the recorded deviations; divide the path previously passed by the end-effector into one or more passed regions, and compute the cumulative deviation in each of the one or more passed region using the POSE deviations within each of the one or more passed regions; determine at least one re-pass region, where the re-pass region is defined as a passed region having cumulative deviation outside predefined criteria; and instruct the surgical robot to perform a subsequent pass with the end-effector in the at least one re-pass region to resurface the tissue. In particular inventive embodiments, the software instructions that instruct the surgical robot to perform a subsequent pass with the end-effector is only executed if the user provides input to do so (i.e., requiring user acknowledgement before instructing the surgical robot to perform a subsequent pass). The robotic surgical system 200 may further include a graphical user interface displayed on a monitor 222 in the OR. The software executable instructions when executed by the processor may further display the POSE deviations and/or computed cumulative deviations to the user in real-time, and provide options for the user to set and/or adjust the predefined criteria to a particular threshold deviation that dictates whether the surgical robot should resurface a passed region or cut path. The executable instructions may further cause the GUI to display which passed regions of resected tissue are not meeting the threshold deviation, and may display a newly achieved surface profile after resurfacing. The executable instructions may further cause the GUI to provide the user with options to decide whether the achieved deviation profile is good enough, or whether to spend additional time with resurfacing one or more regions of previously resected tissue.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A surgical system for resecting tissue, the system comprising:
   a surgical robot comprising an end-effector configured to remove a tissue at planned end-effector position; and
   a computing system comprising one or more processors configured to:
      record an end-effector position to generate a recorded end-effector position while the end-effector removes a tissue at the recorded end-effector position;
      determine a deviation between the recorded end-effector position and the planned end-effector position; and
      compare the deviation against pre-defined criteria,
      wherein, when the deviation meets or exceeds the pre-defined criteria, the computing system is further configured to:
         instruct the surgical robot to revisit a passed region previously passed by the end-effector; and
         remove a tissue with the end-effector at a location adjacent to the recorded end-effector position so that the end-effector resurfaces the tissue of the passed region,
      wherein the end-effector is operated with first operating conditions while removing the tissue at the recorded end-effector position and second operating conditions while removing the tissue at the location adjacent to the recorded end-effector position to resurface the tissue of the passed region, and
      wherein the first operating conditions are different from the second operating conditions in a speed of the end-effector, a direction of motion by the end-effector or an offset in the recorded end-effector position.

2. The system of claim 1, wherein the pre-defined criteria comprise (i) a maximum deviation; (ii) a mean deviation; or (iii) a threshold deviation.

3. The system of claim 1, wherein the computing system is further configured to receive user input before the surgical robot is instructed to the passed region previously passed by the end-effector.

4. The system of claim 1, wherein the computing system is further configured to determine a cumulative deviation between at least a portion of the recorded end-effector position and at least a portion of the planned end-effector position and compare the cumulative deviation to the pre-defined criteria.

5. The system of claim 1, wherein the pre-defined criteria comprise (i) a maximum cumulative error; (ii) a mean cumulative error; (iii) a threshold error; or (iv) a standard deviation threshold.

6. The system of claim 1, wherein the computing system is further configured to determine a first cumulative deviation for a recorded end-effector position in a first region and a second cumulative deviation for a recorded end-effector position in a second region and compare the first cumulative deviation and the second cumulative deviation to the pre-defined criteria.

7. The system of claim 6, wherein the computing system is further configured to instruct the surgical robot to remove a tissue with the end-effector at a location adjacent to the recorded end-effector position in the first region or the second region if the first cumulative deviation or the second cumulative deviation meets or exceeds the pre-defined criteria.

8. The system of claim 7, wherein the computing system is further configured to receive user input before the surgical robot is instructed to remove the tissue with the end-effector at the location adjacent to the recorded end-effector position in the first region or the second region.

9. A method for resecting tissue with a surgical robot comprising an end-effector, the method comprising:
   recording an end-effector position to generate a recorded end-effector position while the end-effector removes a tissue at the recorded end-effector position;
   determining a deviation between the recorded end-effector position and a planned end-effector position; and
   comparing the deviation against pre-defined criteria,
      wherein, when the deviation meets or exceeds the pre-defined criteria, the surgical robot is instructed to revisit a passed region previously passed by the end-effector and to remove a tissue with the end-effector at a location adjacent to the recorded end-effector position so that the end-effector resurfaces the tissue of the passed region,
      wherein the end-effector is operated with first operating conditions while removing the tissue at the recorded end-effector position and second operating conditions while removing the tissue at the location adjacent to the recorded end-effector position to resurface the tissue of the passed region, and
      wherein the first operating conditions are different from the second operating conditions in a speed of the end-effector, a direction of motion by the end-effector or an offset in the recorded end-effector position.

10. The method of claim 9, wherein the pre-defined criteria comprises (i) a maximum deviation; (ii) a mean deviation; or (iii) a threshold deviation.

11. The method of claim 9, further comprising determining a cumulative deviation between at least a portion of the recorded end-effector position and at least a portion of the planned end-effector position and comparing the cumulative deviation to the pre-defined criteria.

12. The method of claim 11, wherein the pre-defined criteria comprises (i) a maximum cumulative error; (ii) a mean cumulative error; (iii) a threshold error; or (iv) a standard deviation threshold.

13. The method of claim 11, further comprising:
determining a first cumulative deviation for a recorded end-effector position in a first region and a second cumulative deviation for a recorded end-effector position in a second region and comparing the first cumulative deviation and the second cumulative deviation to the pre-defined criteria.

14. The method of claim 13, further comprising instructing the surgical robot to remove a tissue with the end-effector at a location adjacent to the recorded end-effector position in the first region or the second region if the first cumulative deviation or the second cumulative deviation meets or exceeds the pre-defined criteria.

* * * * *